United States Patent
Lee et al.

(10) Patent No.: US 12,017,209 B2
(45) Date of Patent: Jun. 25, 2024

(54) SPARGER AND REACTOR COMPRISING THE SAME

(71) Applicant: LG CHEM, LTD., Seoul (KR)

(72) Inventors: Hong Min Lee, Daejeon (KR); Moon Sub Hwang, Daejeon (KR); Min Ho Sun, Daejeon (KR); Jong Hun Song, Daejeon (KR); Kyung Seog Youk, Daejeon (KR); Jeong Seok Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 205 days.

(21) Appl. No.: 17/772,086

(22) PCT Filed: Jul. 22, 2021

(86) PCT No.: PCT/KR2021/009463
§ 371 (c)(1),
(2) Date: Apr. 26, 2022

(87) PCT Pub. No.: WO2022/059904
PCT Pub. Date: Mar. 24, 2022

(65) Prior Publication Data
US 2022/0379277 A1  Dec. 1, 2022

(30) Foreign Application Priority Data
Sep. 17, 2020  (KR) .......... 10-2020-0119901

(51) Int. Cl.
*B01J 19/24* (2006.01)
*B01J 4/00* (2006.01)
*B01J 8/44* (2006.01)
*B01J 19/06* (2006.01)
*C07C 2/08* (2006.01)

(52) U.S. Cl.
CPC ............... *B01J 4/004* (2013.01); *B01J 19/06* (2013.01); *B01J 19/24* (2013.01); *B01J 2204/002* (2013.01); *C07C 2/08* (2013.01)

(58) Field of Classification Search
CPC ... B01J 4/004; B01J 19/06; B01J 19/24; B01J 2204/002; B01J 8/22; B01J 8/44; B01J 10/00; B01J 10/002; C07C 2/08
USPC ........................................................ 422/131
See application file for complete search history.

(56) References Cited

U.S. PATENT DOCUMENTS 6,113,862 A    9/2000  Jorgensen et al.
2015/0291989 A1  10/2015  Kim et al.

FOREIGN PATENT DOCUMENTS

| CN | 205046110 U | 2/2016 |
| CN | 106582459 A | 4/2017 |
| CN | 206715895 U | 12/2017 |

(Continued)

OTHER PUBLICATIONS

Gemello, et al. 2018. Hydrodynamics and Bubble Size in Bubble Columns: Effects of Contaminants and Spargers. Chemical Engineering Science. vol. 184, Jul. 20, 2018, pp. 93-102.

*Primary Examiner* — Huy Tram Nguyen
(74) *Attorney, Agent, or Firm* — Bryan Cave Leighton Paisner LLP

(57) ABSTRACT

Provided are a sparger including: a disc-shaped body; and a first hole and a second hole having different sizes from each other provided in the body, wherein a diameter of the second hole is smaller than a diameter of the first hole, and a reactor comprising the sparger.

9 Claims, 4 Drawing Sheets

(56) References Cited

FOREIGN PATENT DOCUMENTS

| | | | | |
|---|---|---|---|---|
| CN | 110652943 | A | 1/2020 | |
| CN | 110913982 | A | 3/2020 | |
| EP | 0 684 871 | B1 | 5/1998 | |
| EP | 1777000 | A1 * | 4/2007 | ............ B01J 10/002 |
| JP | 09-136029 | A | 5/1997 | |
| JP | 10-152463 | A | 6/1998 | |
| JP | 11-501566 | A | 2/1999 | |
| JP | 2014-500251 | A | 1/2014 | |
| JP | 2019-536626 | A | 12/2019 | |
| KR | 10-0130715 | B1 | 11/1997 | |
| KR | 10-2012-0078350 | A | 7/2012 | |
| KR | 10-2014-0124457 | A | 10/2014 | |
| KR | 10-2016-0013672 | A | 2/2016 | |
| KR | 10-2017-0004933 | A | 1/2017 | |
| KR | 10-1863390 | B1 | 7/2018 | |
| KR | 10-2019-0110958 | A | 10/2019 | |
| KR | 10-2019-0132118 | A | 11/2019 | |
| KR | 1020190132118 | A | 11/2019 | |
| WO | 9847611 | A1 | 10/1998 | |
| WO | 2015016060 | A1 | 2/2015 | |
| WO | 2019/138453 | A1 | 7/2019 | |

\* cited by examiner

【FIG. 1】
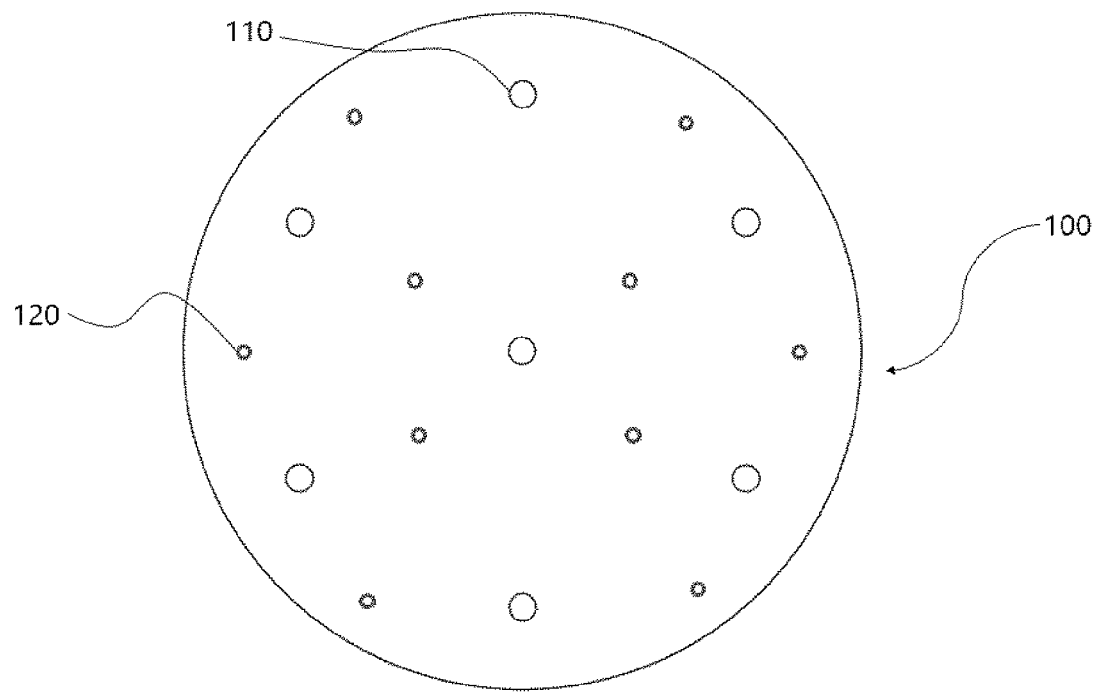
【FIG. 2】
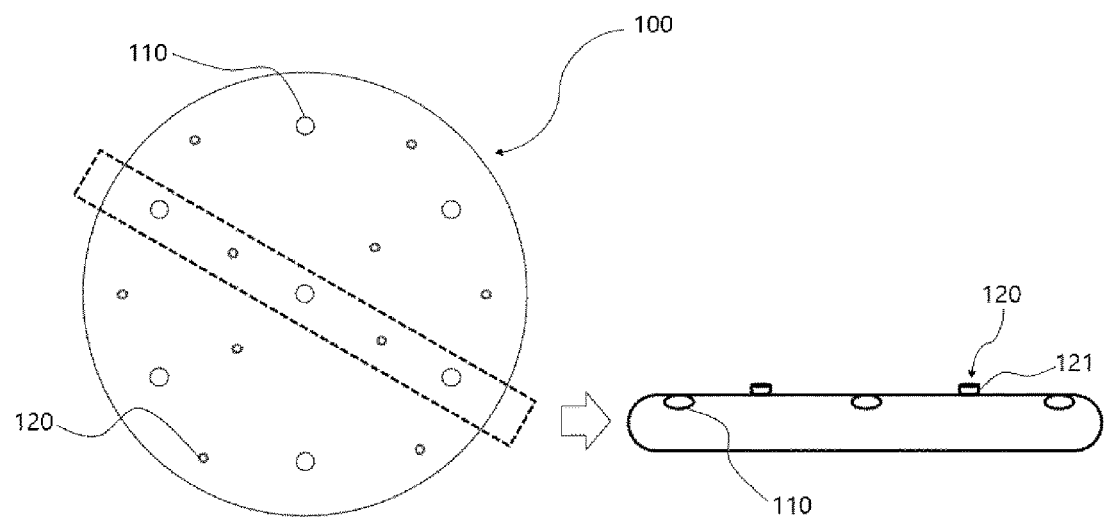

[FIG. 3]
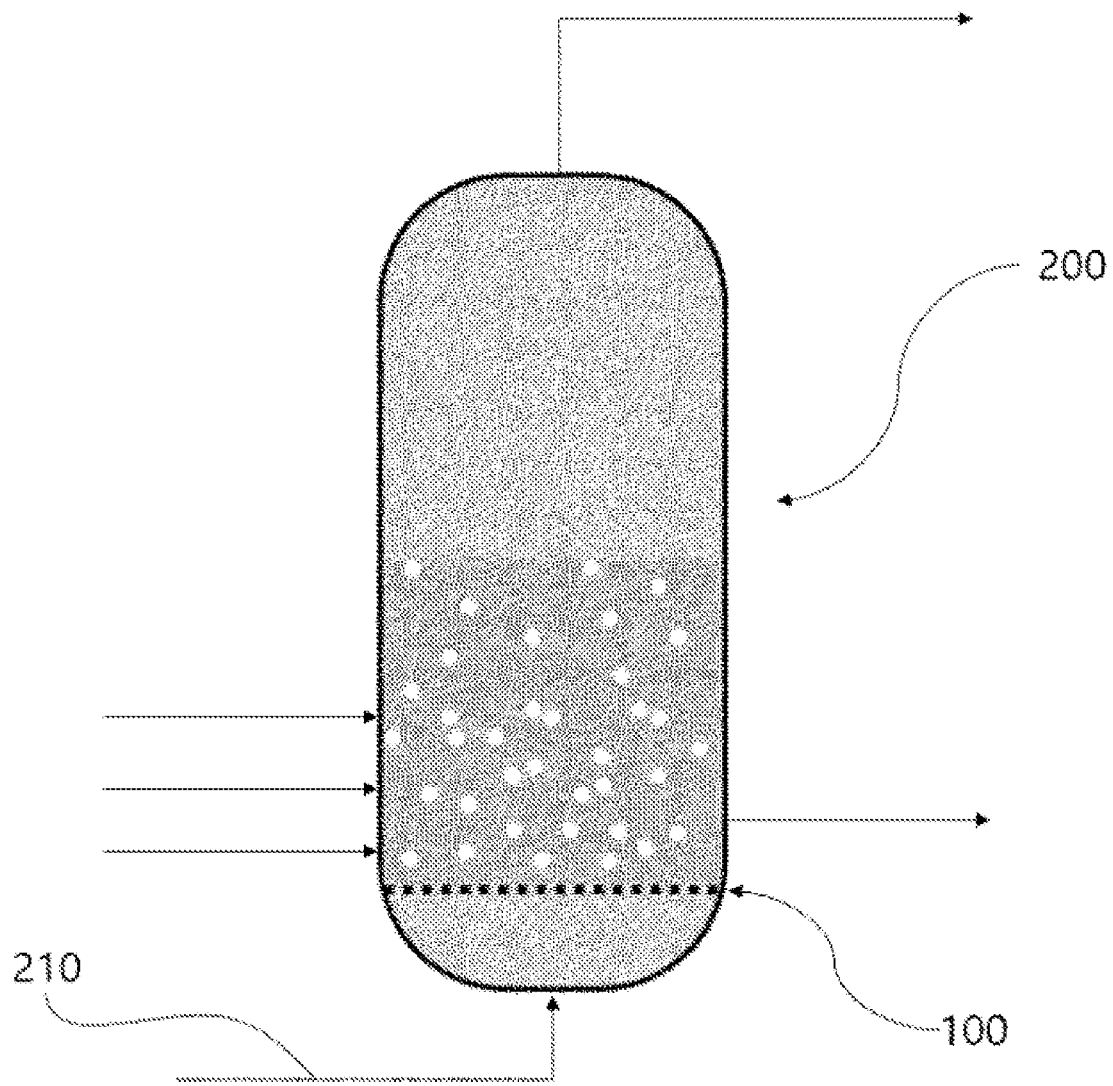

[FIG. 4]
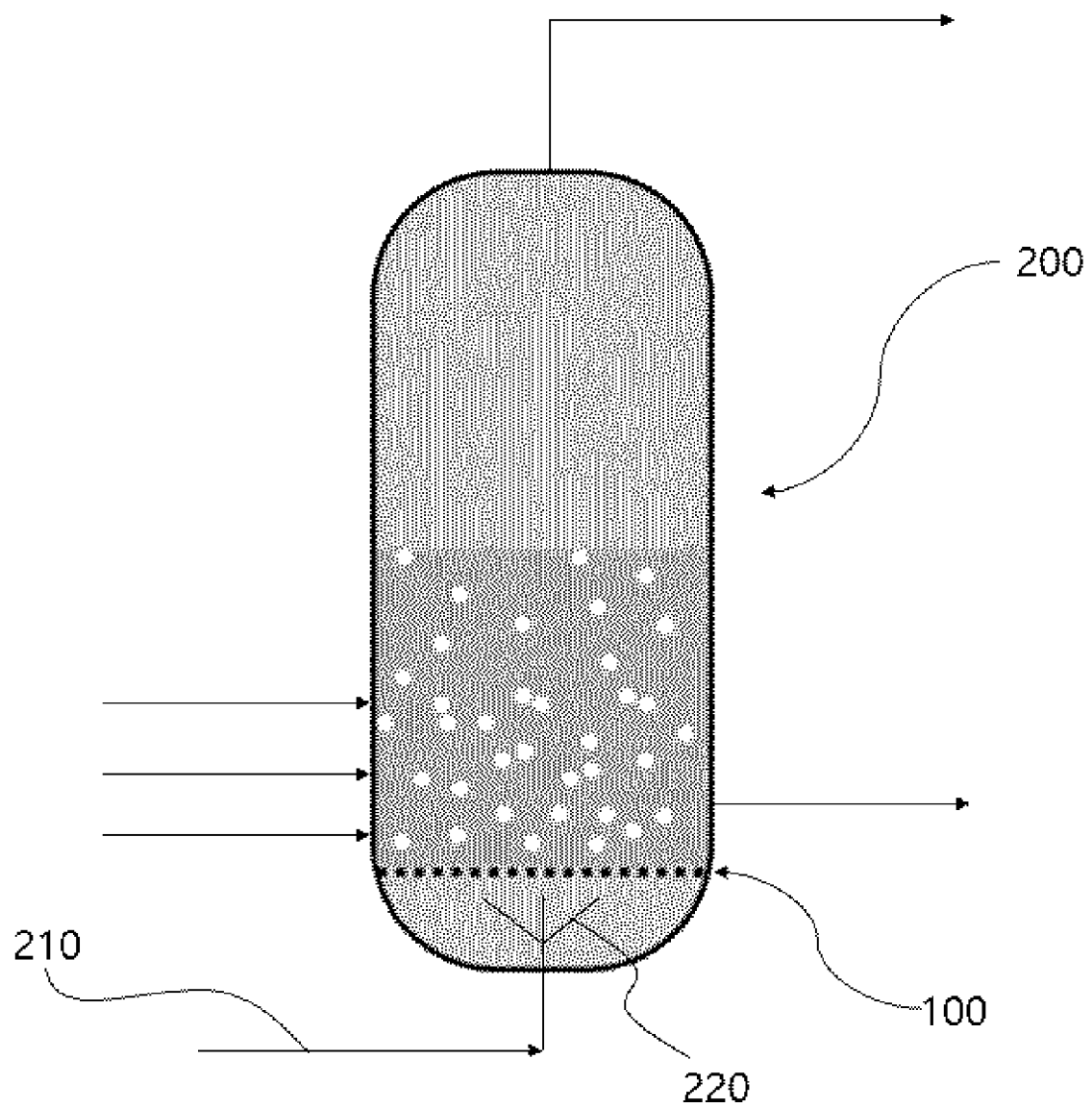

【FIG. 5】
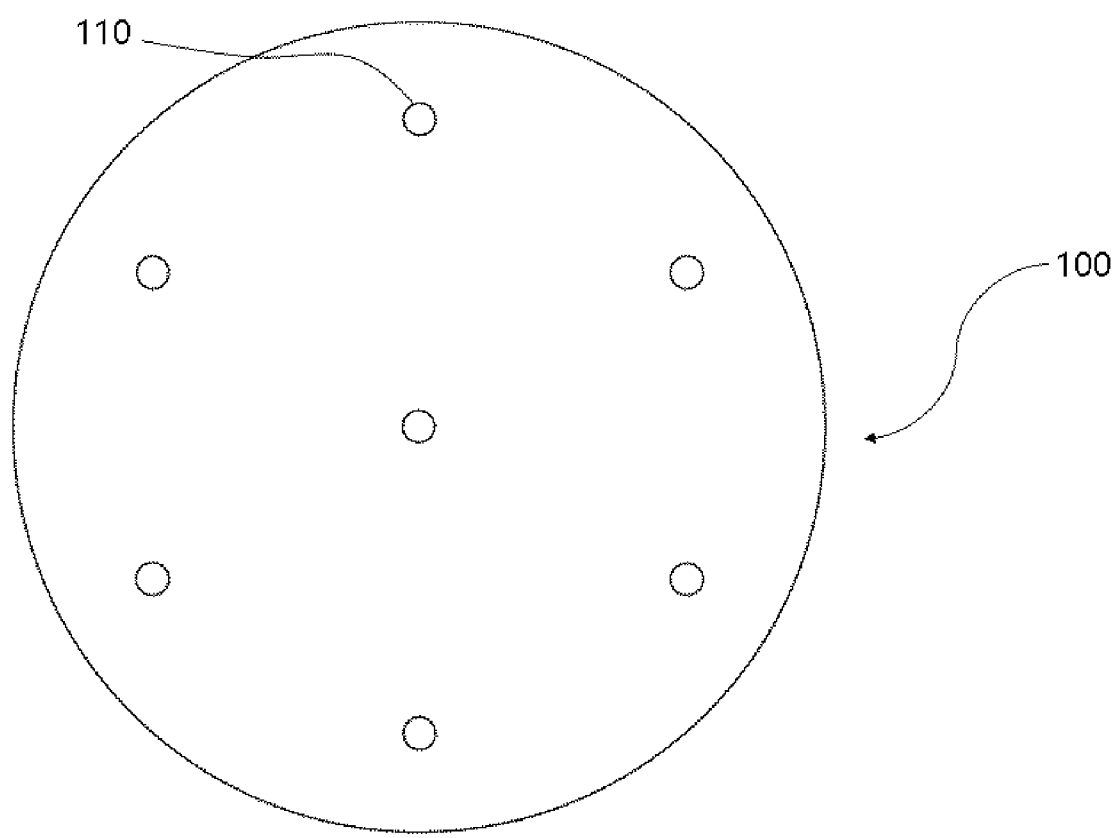

SPARGER AND REACTOR COMPRISING THE SAME

CROSS-REFERENCE TO RELATED APPLICATIONS

The present application is a National Phase entry pursuant to 35 U.S.C. § 371 of International Application No. PCT/KR2021/009463, filed on Jul. 22, 2021, and claims the benefit of and priority to Korean Patent Application No. 10-2020-0119901, filed on Sep. 17, 2020, the entire contents of which are incorporated by reference in their entirety for all purposes as if fully set forth herein.

TECHNICAL FIELD

The present invention relates to a sparger, and more particularly, to a sparger which may improve both a mixing effect and a fouling prevention effect and a reactor comprising the same.

BACKGROUND ART

An α-olefin (alpha-olefin) is an important material which is used in comonomers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE).

The α-olefins such as 1-hexene and 1-octene are produced representatively by an oligomerization reaction of ethylene. The ethylene oligomerization reaction is performed by an oligomerization reaction (trimerization reaction or tetramerization reaction) of ethylene in the presence of a catalyst by using ethylene as a reactant, and the product produced by the reaction includes not only a multi-component hydrocarbon mixture including 1-hexene and 1-octene to be desired but also a small amount of by-products including a polymer material of C20+ during a catalytic reaction. Fouling in which holes of a sparger are blocked may occur due to the by-products, and thus, a mixing efficiency is decreased and maintenance costs are incurred.

DISCLOSURE

Technical Problem

An object of the present invention is to provide a sparger which is designed to increase a mixing efficiency and to decrease a fouling occurrence, and a reactor comprising the sparger, in order to solve the above problems mentioned in Background Art.

Technical Solution

In one general aspect, a sparger includes: a body; and a first hole and a second hole having different sizes from each other provided in the body, wherein a diameter of the second hole is smaller than a diameter of the first hole.

In another general aspect, a reactor includes: a monomer supply line to which a gaseous monomer stream is supplied; and the above sparger for dispersing the gaseous monomer stream supplied through the monomer supply line.

Advantageous Effects

According to the sparger of the present invention, a first hole and a second hole having different sizes from each other are provided in a body and a diameter of the second hole is formed to be smaller than a diameter of the first hole, thereby improving a mixing efficiency and extending a wash cycle.

In addition, the present invention is provided with a protrusion in the second hole provided in the sparger, thereby minimizing fouling of the second hole.

DESCRIPTION OF DRAWINGS

FIG. 1 is a plan view showing a sparger according to an exemplary embodiment of the present invention.

FIG. 2 is a plan view and a cross-sectional view showing the sparger according to an exemplary embodiment of the present invention.

FIG. 3 is a process flow diagram showing a reactor according to an exemplary embodiment of the present invention.

FIG. 4 is a process flow diagram showing a reactor according to an exemplary embodiment of the present invention.

FIG. 5 is a plan view showing a sparger according to the Comparative Example.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "stream" may refer to a fluid flow in the process, or may refer to the fluid itself flowing in a moving line (pipe). Specifically, the "stream" may refer to both a fluid itself flowing in a pipe connecting each device and a fluid flow. In addition, the fluid may refer to inclusion of any one or more of gas, liquid, and solid.

In the present invention, "C#", in which "#" is a positive integer, represents all hydrocarbons having #carbon atoms. Therefore, the term "C10" represents a hydrocarbon compound having 10 carbon atoms. In addition, the term "C#+" represents all hydrocarbon molecules having #or more carbon atoms. Therefore, the term "C10+" represents a mixture of hydrocarbons having 10 or more carbon atoms.

Hereinafter, the present invention will be described in more detail referring to the following FIGS. 1 to 4, for better understanding of the present invention.

According to the present invention, a sparger 100 is provided. The sparger 100 may have a disc-shaped body; and a first hole 110 and a second hole 120 having different sizes from each other provided in the body, as shown in FIG. 1.

According to an exemplary embodiment of the present invention, the sparger 100 is, for example, provided in a lower portion of the reactor 200 to disperse a gaseous monomer stream supplied to the reactor 200 upward, to mix a liquid reaction medium in the reactor 200, and to improve a conversion rate of the monomer.

The body of the sparger 100 may be freely designed depending on the shape of the reactor 200, and for example, the body of the sparger 100 may be formed in a disc shape having an outer circumferential surface having the same structure as the inner surface of the reactor 200. Here, the outer circumferential surface of the body may be designed to be closely adhered to the inner surface of the reactor 200.

A diameter of the body may be, for example, 100 mm to 1500 mm, 100 mm to 1000 mm, or 100 mm to 500 mm, and a thickness of the body may be, for example, 0 mm to 100 mm, 1 mm to 50 mm, or 10 mm to 30 mm.

According to an exemplary embodiment of the present invention, the body of the sparger 100 may include a first hole 110 and a second hole 120 having different sizes from each other. Here, a diameter of the second hole 120 may be smaller than a diameter of the first hole 110. For example, the first hole 110 provided in the body of the sparger 100 may be already formed in the sparger 100, and the second hole 120 having a smaller diameter than the first hole 110 may be further formed.

A plurality of first holes 110 may be formed at equal intervals in the center and along the circumference of the body. Specifically, a gaseous monomer stream may be uniformly sprayed into the reactor 200 through the first hole 110 formed at equal intervals in the center and along the circumference of the body.

The diameter of the first hole 110 may be, for example, 1 mm to 150 mm, 1 mm to 130 mm, or 1 mm to 50 mm. In addition, the diameter of the first hole 110 may be 1% to 50%, 1% to 30%, or 1% to 10% of the diameter of the body. The first hole 110 is provided to satisfy the above conditions, thereby preventing a fouling occurrence in the first hole 110 and spraying the gaseous monomer stream into the liquid reaction medium in the reactor 200 to be mixed with the liquid reaction media in the reactor 200.

In addition, the second hole 120 has a smaller diameter than the first hole 110 and may be formed in an area between the first holes 110. For example, the second hole 120 may be formed in any one or more areas between the first hole 110 formed in the center of the body and the first hole 110 formed in the circumference or between the first holes 110 formed at equal intervals along the circumference. As a specific example, a plurality of second holes 120 may be formed in each area between the first hole 110 formed in the center of the body and the first hole 110 formed in the circumference or between the first holes 110 formed at equal intervals along the circumference. Thus, a mixing efficiency in the reactor is increased and accumulation of by-products in the second hole 120 due to a high-volume flow rate of gas is prevented, thereby lowering a possibility of fouling in the sparger to further extend a wash cycle of the reactor 200.

The diameter of the second hole 120 may be, for example, 1 mm to 100 mm, 1 mm to 50 mm, or 1 mm to 10 mm. In addition, the diameter of the second hole 120 may be 0.1% to 40%, 0.1% to 25%, or 1% to 10% of the diameter of the body. The second hole 120 is provided to satisfy the above conditions, thereby allowing even a portion which is not mixed with the first hole 110 having a larger diameter to be mixed and increasing a mixing efficiency of the liquid reaction medium in the reactor 200.

In addition, the diameter of the second hole 120 may be 1% to 40%, 5% to 40%, or 10% to 30% of the diameter of the first hole 110. A ratio between the diameter of the second hole 120 and the diameter of the first hole 110 is formed to be in the above range, thereby preventing shutdown of the reactor due to the fouling in the sparger, and also increasing the mixing efficiency in the reactor to minimize a dead volume, so that an effect of increasing a reaction conversion rate may be obtained.

However, when a diameter is relatively small like the second hole 120, the mixing efficiency of the reaction medium in the reactor 200 may be increased, but a possibility of fouling is increased as compared with the first hole 110 having a relatively large diameter. However, even in the case in which the second hole 120 is fouled, the reaction may be performed by the first hole 110, and thus, a wash cycle in which the reactor 200 should be shut down and the inside of the reactor 200 and devices such as the sparger 100 should be washed may be extended.

According to an exemplary embodiment of the present invention, the second hole 120 may include a protrusion 121 formed upward along the outer circumferential surface, as shown in FIG. 2. Specifically, the second hole 120 has a higher possibility of fouling than the first hole 110 due to its smaller diameter, but the protrusion 121 is formed in the second hole 120, thereby producing a height difference from the first hole 110, and preventing accumulation of by-products due to an increased volume flow rate of gas passing through the first hole 110, so that a possibility of fouling in the sparger is lowered to further extend the wash cycle of the reactor 200.

A height of the protrusion 121 formed upward along the outer circumferential surface of the second hole may be 5% to 40%, 10% to 40%, or 10% to 30% of the thickness of the body. The protrusion 121 is formed at the height in the above range, thereby having a height difference from the first hole 110 to prevent fouling in the second hole 120 by the by-products accumulated in the sparger, and thus, to extend a shutdown cycle of the reactor.

The protrusion 121 may be formed in a structure having a constant diameter upward. Specifically, the protrusion 121 has a structure protruding upward from the outer circumferential surface of the second hole 120 with a constant height, and may be formed in a structure having a constant diameter upward from the protrusion 121. Thus, a linear velocity of the gaseous monomer stream passing through the sparger and being supplied to the reactor is maintained constant, while a possibility of fouling occurrence may be lowered.

According to the present invention, a reactor 200 including the sparger 100 is provided. Specifically, in FIG. 3, the reactor 200 may include a monomer supply line 210 to which the gaseous monomer stream is supplied; and the sparger 100 according to the present invention for dispersing the gaseous monomer stream supplied through the monomer supply line 210.

According to an exemplary embodiment of the present invention, the reactor 200 may be a reactor appropriate for a continuous process. For example, the reactor 200 may include any one or more reactors selected from the group consisting of a continuous stirred-tank reactor, a plug flow reactor, and a bubble column reactor. As a specific example, the reactor 200 may be a bubble column reactor. Thus, the monomer may be continuously reacted.

According to an exemplary embodiment of the present invention, the reactor 200 may be for producing an oligomer by oligomerizing a monomer in the presence of a catalyst and a solvent.

The monomer may include ethylene. Specifically, a gaseous monomer stream including an ethylene monomer is introduced into the reactor 200 through a monomer supply line 210 provided in a lower portion of the reactor 200, the gaseous monomer stream is dispersed by the sparger 100 to be oligomerized in a reaction medium in the reactor 200, thereby producing an α-olefin product to be desired.

According to an exemplary embodiment of the present invention, a spray unit 220 provided to be extended from the monomer supply line may be further included, as shown in FIG. 4. A gaseous ethylene monomer transferred through the monomer supply line 210 may be sprayed through the spray unit 220 to pass through the sparger 100.

The spray unit 220 may be formed to be extended from the monomer supply line 210 to branch into multiple pipes, and a spray nozzle may be formed at the end of each of the branched multiple pipes. Specifically, the gaseous ethylene monomer transferred through the monomer supply line 210 may be introduced to the reactor 200 through the spray nozzle of the spray unit 220. As such, the gaseous ethylene monomer introduced to the reactor 200 may pass through the sparger 100 and be sprayed upward from the reactor 200. As such, since the spray unit 220 is provided, no additional apparatus such as a conventional deflector is needed, and when the conventional deflector is used, a difficulty in maintaining a linear velocity constant of the gaseous monomer stream may be solved. As such, the linear velocity of the gaseous monomer stream is maintained constant, whereby a dispersion degree of a reaction solution and by-products in the reactor may be maintained uniform and accumulation of the by-products on one side may be prevented.

The oligomerization reaction is carried out in a lower or a middle area of the reactor 200, and the oligomerization reaction of the monomer may be carried out in a liquid state being dissolved in a solvent in the presence of a catalyst and a cocatalyst.

The oligomerization reaction may refer to a reaction in which a monomer is oligomerized. The oligomerization may be referred to as trimerization or tetramerization depending on the number of monomers to be polymerized, and these are collectively called multimerization.

In the oligomerization reaction of the monomer, an unreacted monomer and a vaporized solvent in the reactor 200 may be discharged to the upper portion of the reactor 200, and may be circulated to the reactor 200 and reused in the oligomerization reaction of the monomer. In addition, the oligomer produced by the oligomerization reaction of the monomer may be separated through the lower side of the reactor 200 and obtained.

The α-olefin, which is an important material used in copolymers, cleaning agents, lubricants, plasticizers, and the like, is commercially widely used, and in particular, 1-hexene and 1-octene are often used as a comonomer for adjusting the density of polyethylene in the production of linear low-density polyethylene (LLDPE). The α-olefin such as 1-hexene and 1-octene may be produced by, for example, a trimerization reaction or tetramerization reaction of an ethylene monomer.

The oligomerization reaction of the monomer may be carried out by a homogeneous liquid phase reaction, a slurry reaction in which the catalyst is in the form of being partially not dissolved or not dissolved at all, a two-phase liquid/liquid reaction, or a bulk phase reaction or gas phase reaction of which the product acts as a main medium, in the presence or absence of a solvent, by applying the reaction system and a common contact technology.

The solvent, the catalyst, and the cocatalyst may be supplied in a liquid phase to the lower side of the reactor 200.

The catalyst may include a transition metal source. The transition metal source may be, for example, a compound including one or more selected from the group consisting of chromium (III) acetylacetonate, chromium (III) chloride tetrahydrofuran, chromium (III) 2-ethylhexanoate, chromium (III) tris(2,2,6,6-tetramethyl-3,5-heptanedionate), chromium (III) benzoylacetonate, chromium (III) hexafluoro-2,4-pentanedionate, chromium (III) acetatehydroxide, chromium (III) acetate, chromium (III) butyrate, chromium (III) pentanoate, chromium (III) laurate, and chromium (III) stearate.

The cocatalyst may include, for example, one or more selected from the group consisting of trimethyl aluminum, triethyl aluminum, triisopropyl aluminum, triisobutyl aluminum, ethylaluminum sesquichloride, diethylaluminum chloride, ethyl aluminum dichloride, methylaluminoxane, modified methylaluminoxane, and borate.

The solvent used in the oligomerization reaction of the monomer may include one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene.

As such, in the process of oligomerizing a monomer in the presence of the catalyst and the solvent, by-products such as cohesive by-products for example a polymer are produced in addition to an oligomer product. The by-products may block holes formed in the sparger 100 to cause fouling.

Regarding this, the reactor 200 according to the present invention uses the sparger 100 according to the present invention described above, thereby preventing blockage of the holes in the sparger due to the fouling to extend the wash cycle of the reactor 200, and thus, preventing a production decrease due to a decreased operation time and reducing costs required in the wash process.

According to an exemplary embodiment of the present invention, in the reactor 200, an apparatus required for oligomer production such as a valve, a condenser, a reboiler, a pump, a cooling facility, a filter, an agitator, a compressor, and a mixer may be further installed, if necessary.

Hereinabove, the sparger according to the present invention and the reactor comprising the same have been described and illustrated in the drawings; however, the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for using the sparger according to the present invention and the reactor comprising the same.

Hereinafter, the present invention will be described in more detail by the Examples. However, the following Examples are provided for illustrating the present invention, and it is apparent to a person skilled in the art that various modifications and alterations may be made without departing from the scope and spirit of the present invention and the scope of the present invention is not limited thereto.

EXAMPLES

Example 1

The sparger 100 according to FIG. 1 was provided in a bubble column reactor 200 to perform an oligomerization reaction of an ethylene monomer, as shown in FIG. 3. Specifically, a solvent, a catalyst, and a cocatalyst were supplied to a lower side of the reactor 200, a gaseous ethylene monomer was supplied through a monomer supply line 210 and a spray unit 220 provided in a lower portion of the reactor 200, and the sparger 100 was used to disperse the stream upward to perform an oligomerization reaction in a liquid reaction medium in the reactor 200. An α-olefin produced by the oligomerization reaction was separated in the lower side of the reactor 200 and obtained, and an unreacted monomer and a vaporized solvent were discharged to an upper portion of the reactor 200.

Here, a diameter of the body of the sparger 100 was 300 mm, the thickness of the body of the sparger 100 was 20 mm, the diameter of a first hole 110 of the sparger 100 was 20 mm, and the diameter of a second hole 120 of the sparger 100 was 5 mm.

In this case, a mixing efficiency of the ethylene monomer was increased to increase the production of the α-olefin. In addition, fouling occurrence in the sparger 100 was decreased to extend a shutdown cycle for washing the reactor 200.

Example 2

The process was performed in the same manner as in Example 1, except that a sparger 100 having a protrusion 121 having a constant diameter formed upward along the outer circumferential surface of the second hole was used, as shown in FIG. 2, as the sparger 100. At this time, the height of the protrusion 121 was formed to be 5 mm.

In this case, the mixing efficiency of the ethylene monomer was increased to increase the production of the α-olefin, as in Example 1. In addition, a possibility of fouling occurrence in the second hole 120 which is likely to cause fouling is decreased due to the protrusion 121 to decrease fouling occurrence in the sparger 100, thereby extending a shutdown cycle for washing the reactor 200, as compared with Example 1.

Example 3

The process was performed in the same manner as in Example 2, except that a spray unit 220 was provided to spray the gaseous ethylene monomer through the spray unit 220 so that the monomer was supplied to pass through the sparger 100, as shown in FIG. 4.

In this case, the mixing efficiency of the ethylene monomer was increased as in Example 2 to increase the production of an α-olefin, and a fouling occurrence of the sparger 100 was decreased to extend the shutdown cycle for washing the reactor 200. Also, it was confirmed that the spray unit 220 was used to maintain a linear velocity of the gaseous ethylene monomer supplied to the reactor 200 constant to maintain a dispersion degree of the reaction solution and the by-products in the reactor constant, thereby preventing accumulation of the by-products on one side.

Comparative Example

Comparative Example 1

The process was performed in the same manner as in Example 1, except that a sparger 100 having only a first hole 110 formed was used, as shown in FIG. 5, as the sparger 100.

In this case, it was confirmed that the mixing efficiency of the ethylene monomer was decreased as compared with Examples 1 to 3 to decrease the production of an α-olefin, and a fouling occurrence rate in the sparger 100 was increased to shorten the shutdown cycle for washing the reactor 200.

The invention claimed is:

1. A sparger comprising:
   a body; and
   a first hole and a second hole having different sizes from each other provided in the body,
   wherein a diameter of the second hole is smaller than a diameter of the first hole,
   wherein the second hole includes a protrusion formed upward along an outer circumference surface of the second hole, and
   wherein the protrusion is formed to have a constant diameter upward.

2. The sparger of claim 1, wherein the body has a disc shape,
   wherein the sparger comprises a plurality of the first holes and a plurality of the second holes;
   wherein the first holes are formed at equal intervals in a center and along a circumference of the body, and
   wherein the second holes are formed in an area between the first holes.

3. The sparger of claim 2, wherein the diameter of the first hole is 1 mm to 150 mm, and the diameter of the second hole is 1 mm to 100 mm.

4. The sparger of claim 2, wherein the diameter of the second hole is 1% to 40% of the diameter of the first hole.

5. The sparger of claim 2, wherein the diameter of the first hole is 1% to 50% of a diameter of the body, and the diameter of the second hole is 0.1% to 40% of the diameter of the body.

6. The sparger of claim 1, wherein a height of the protrusion is 5% to 40% of a thickness of the body.

7. A reactor comprising:
   a monomer supply line to which a gaseous monomer stream is supplied; and
   the sparger of claim 1 for dispersing the gaseous monomer stream supplied through the monomer supply line.

8. The reactor of claim 7, further comprising: a spray unit provided to be extended from the monomer supply line.

9. The reactor of claim 7, wherein the gaseous monomer includes an ethylene monomer and the reactor performs an oligomerization reaction of the ethylene monomer.

* * * * *